United States Patent [19]

Suami

[11] 4,220,643
[45] Sep. 2, 1980

[54] NITROSOUREA PENTOSE COMPOUNDS

[76] Inventor: Tetsuo Suami, 5-8, Nakamachi 3-chome, Musashino-shi, Tokyo, Japan

[21] Appl. No.: 951,456

[22] Filed: Oct. 16, 1978

[30] Foreign Application Priority Data

Oct. 27, 1977 [JP] Japan .................. 52/128086

[51] Int. Cl.$^2$ .................. A61K 31/70; C07H 5/06
[52] U.S. Cl. .................. 424/180; 536/18; 536/22; 536/53
[58] Field of Search .................. 536/53, 18, 22; 424/180

[56] References Cited

U.S. PATENT DOCUMENTS

| | | | |
|---|---|---|---|
| 3,767,640 | 10/1973 | Suami et al. | 536/4 |
| 3,940,383 | 2/1976 | Fujiwara et al. | 536/4 |
| 4,057,684 | 11/1977 | Kimura et al. | 536/53 |
| 4,086,415 | 4/1978 | Suami et al. | 536/4 |

OTHER PUBLICATIONS

Johnson et al., "Cancer Treatment Reviews," (1975), 2, pp. 1-31.

*Primary Examiner*—Johnnie R. Brown
*Attorney, Agent, or Firm*—Haight, Rosfeld, Noble & Santa Maria

[57] ABSTRACT

Novel nitrosourea compounds are provided which possess a high level of inhibitory activity against leukemia and tumors with a low toxicity and which are therefore useful for pharmaceutical purposes. The compounds have the chemical structure:

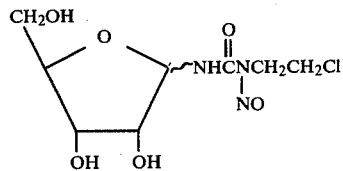

wherein ~ represents a single bond which may be in the α- or β-position and are prepared by nitrosating a urea compound of the formula:

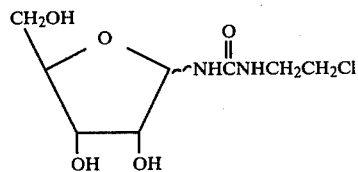

with a nitrosating agent in a manner known per se.

4 Claims, No Drawings

NITROSOUREA PENTOSE COMPOUNDS

BACKGROUND OF THE INVENTION

This invention relates to novel nitrosourea compounds which possess a high level of inhibitory activity against leukemia and tumors with a low toxicity and which are therefore useful in the therapeutic treatments of leukemia and tumors. This invention further relates to a process for the preparation of such novel nitrosourea compounds and to their use for pharmaceutical purposes.

There are a variety of compounds which have been proposed as being effective for inhibiting leukemia and tumors, one class of which is nitrosourea derivatives. Among the nitrosourea derivatives, there may be mentioned streptozotocin [N-(N'-methyl-N'-nitroso-carbamoyl)-D-glucosamine] and its derivatives such as methyl glucosaminides as most typical examples (refer to U.S. Pat. No. 3,577,406 and U.S. Pat. No. 3,767,640, for example), but they are not yet satisfactory because of insufficient activity against leukemia and tumors and/or undesirable side effects thereof. Another class of nitrosourea derivatives is glycosyl derivatives of nitrosoureas which I have recently prepared and confirmed to be novel compounds, among which the presently most interesting compound is 1-(2-chloroethyl)-3-($\beta$-D-glucopyranosyl)-1-nitrosourea (abbreviated as GANU) which has a broad spectrum of antitumor activity against a wide variety of experimental tumors with efficacy in cancer chemotherapy (refer to T. Suami et al., U.S. Pat. No. 4,086,415).

BRIEF SUMMARY OF THE INVENTION

I have now found as a result of my continuing investigations that certain specific novel nitrosourea compounds, as hereinafter shown, exhibit a high inhibitory activity against leukemia and tumors with a low toxicity as evidenced by in vivo tests.

According to one aspect of this invention, therefore, there are provided as novel compounds nitrosourea compounds of the formula:

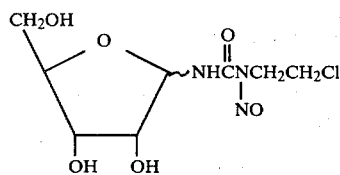

wherein ~ represents a single bond which may be in the $\alpha$- or $\beta$-position, which are designated as 1-(2-chloroethyl)-1-nitroso-3-($\alpha$-D-ribofuranosyl) urea and 1-(2-chloroethyl)-1-nitroso-3-($\beta$-D-ribofuranosyl) urea which are anomers with each other.

DETAILED DESCRIPTION OF THE INVENTION

The two anomers of 1-(2-chloroethyl)-1-nitroso-3-(D-ribofuranosyl) urea according to this invention posses a remarkably high level of activity against leukemia and tumors.

The anti-leukemic activity of both the anomers of this invention was tested on Leukemia L 1210 in mice, details of which are given below. By way of comparison, the 1-methyl homologue of the $\beta$-anomer of this invention, i.e. 1-methyl-1-nitroso-3-($\beta$-D-ribofuranosyl) urea (refer to T. Suami et al., Japanese Patent Prepublication No. 83365/75), was tested in a similar way.

COMPOUNDS

| Compound No. | Name |
| --- | --- |
| 1 | 1-(2-chloroethyl)-1-nitroso-3-($\alpha$-D-ribofuranosyl) urea |
| 2 | 1-(2-chloroethyl)-1-nitroso-3-($\beta$-D-ribofuranosyl) urea |
| 3 | 1-methyl-1-nitroso-3-($\beta$-D-ribofuranosyl) urea (Reference) |

ANIMALS

Male BDF$_1$ mice, aged about 7-weeks old and weighing 22±3 g were used in groups of three animals each for the test of compounds No. 1 and No. 2 or of two animals each for the test of compound No. 3.

TUMOR CELLS

Leukemia L 1210 cells were used. For the test of compounds No. 1 and No. 2, $2 \times 10^6$ cells/0.04 ml/mouse were intraperitoneally inoculated and for the test of compound No. 3, $1.8 \times 10^6/0.04$ ml/mouse were intraperitoneally inoculated.

METHOD

The test compound was dissolved in a physiological salt solution to give a series of solutions in predetermined concentrations and 0.1 ml of the each solution was administered intraperitoneally to each mouse once a day from the 24th hour after the tumor cell inoculation for 3 consecutive days for the test of compounds No. 1 and No. 2 or for 2 consecutive days for the test of compound No. 3. The anti-leukemic activity of the compounds tested was assessed by mean survival days, percentage increase in life-span, number of survivors after 60 days observation and the volume of ascites. The percentage increase in life-span (ILS) was calculated as follows:

$$ILS\ (\%) = (T-C)/C \times 100$$

T: The mean survival days of the treated animals
C: The mean survival days of the untreated animals The control test for this purpose was carried out in the same way as that used for the test of compounds No. 1 and No. 2 or for the test of compound No. 3 except that 0.1 ml of the physiological salt solution was administered in place of the solution of the test compound.

The test results are shown in the following table.

Table

| Anti-leukemic activity of nitrosourea compounds (60 days observation) | | | | |
| --- | --- | --- | --- | --- |
| Compound No. | Dose (mg/kg) | Mean survival days | ILS (%) | Number of survivors (after 60 days) | Volume of ascites (ml) Treated/Control |
| 1 | 16 | 11.3 | 13.0 | 0/3 | 0 |
|   | 8  | >42.3 | >323.0 | 2/3 | 0 |
|   | 4  | >48.3 | >383.0 | 2/3 | 0 |
|   | 2  | 15.3 | 50.0 | 0/3 | 0 |
|   | 1  | 13.7 | 37.0 | 0/3 | 1.7 |
| 2 | 16 | 8.7 | −13.0 | 0/3 | 0 |
|   | 8  | >60.0 | >500.0 | 3/3 | 0 |
|   | 4  | >46.0 | >360.0 | 2/3 | 0 |
|   | 2  | >32.3 | >223.0 | 1/3 | 0 |
|   |    | 15.3 | 53.0 | 0/3 | 2.5 |

Table-continued
Anti-leukemic activity of nitrosourea compounds
(60 days observation)

| Compound No. | Dose (mg/kg) | Mean survival days | ILS (%) | Number of survivors (after 60 days) | Volume of ascites (ml) Treated/Control |
|---|---|---|---|---|---|
| Untreated (control) | — | 10.0 | — | — | 4.5 |
| 3 | 250 | 11.5 | 15.0 | 0/2 | 0.6 |
|   | 200 | 18.0 | 80.0 | 0/2 | 0.3 |
|   | 100 | 15.0 | 50.0 | 0/2 | 0.7 |
|   | 50  | 15.0 | 50.0 | 0/2 | 4.6 |
| Untreated (control) | — | 10.0 | — | — | 5.3 |

It will be clearly appreciated from the above test results that the novel nitrosourea compounds according to this invention show a high value of ILS in a very low dose which is quite unexpected from that of the corresponding methyl homologues and which is a level useful in chemotherapy of transplanted leukemic and tumor diseases.

The nitrosourea compounds according to this invention are further characterized by their low toxicity. Thus, acute toxicity of the compounds in intraperitoneal administration to BDF$_1$ mice is as follows:

|  | LD$_{50}$ |
|---|---|
| 1-(2-chloroethyl)-1-nitroso-3-(α-D-ribofuranosyl) urea | 34 mg/kg |
| 1-(2-chloroethyl)-1-nitroso-3-(β-D-ribofuranosyl) urea | 30 mg/kg |

According to a second aspect of this invention, therefore, there is provided a pharmaceutical composition comprising an effective amount of a nitrosourea compound of the formula (I) in association with a pharmaceutically acceptable excipient, carrier or diluent.

The pharmaceutical composition may be in a form known per se to suit the route of administration that is oral or injection administration for man or oral, injection or intraperitoneal administration for animals. In general, therefore, the pharmaceutical composition may take such form as an ampoule, capsule, tablet, powder, granule and the like to adapt it for oral or injection administration.

This invention also includes as a third aspect thereof a method for the therapeutic treatment of transplanted leukemic and tumor diseases in animals which comprises administering to the animals a therapeutically effective amount, at suitable intervals, of a nitrosourea compound of formula (I) above. It will be appreciated that the amount of the nitrosourea compound to be actually applied will vary dependent upon the particular compound used, the particular composition formulated, the mode of application, the route of administration and other variables. Many factors which modify the action of the drug will be taken into account by those skilled in the art, for example, age, body weight, sex, diet, time of administration, route of administration, rate of metabolism or excretion, drug combination, sensitivities and severity or condition of the disease. Optimal application dose for a given set of conditions can be ascertained by those skilled in the art using conventional tests for the dosage determination in view of the above guidelines.

The novel nitrosourea compounds of formula (I) according to this invention may be prepared simply by nitrosating the corresponding urea compounds in a manner known per se.

According to a fourth aspect of this invention, therefore, there is provided a process for the preparation of nitrosourea compounds of the formula:

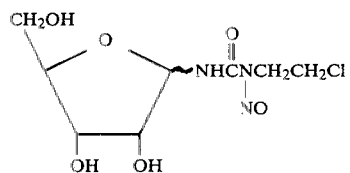 (I)

wherein ~ represents a single bond which may be in the α- or β-position which comprises treating a compound of the formula:

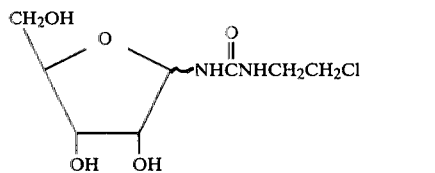 (II)

wherein ~ represents a single bond which may be in the α- or β-position, with a nitrosating agent.

In the process of this invention, the nitrosation reaction may be carried out in a manner known per se. Thus, as the nitrosating agent there may be used an alkali metal nitrite, nitrogen trioxide, dinitrogen tetroxide, nitrosyl chloride and the like as usual. As alkali metal nitrite, e.g. sodium or potassium nitrite, is preferred. The nitrosation reaction may usually be conducted at a temperature of about −10° C. to 30° C. and preferably under acidic conditions, for example, at a pH value of about 1 to 3. As the reaction medium, there may be used the usual organic solvents such as acetone, methanol, ethyl acetate, ether, dioxane and tetrahydrofuran, organic acids such as formic and acetic acids, aqueous solutions of such organic acids and aqueous solutions of inorganic acids such as hydrochloric acid. Under these conditions, completion of the reaction may take about 1 to 12 hours.

By way of explanation, a typical embodiment of the process according to this invention is given wherein 1-(2-chloroethyl)-3-(β-D-ribofuranosyl) urea is used as starting compound. The nitrosation of this starting compound, if carried out under the conditions above-mentioned, usually result in the simultaneous formation of 1-(2-chloroethyl)-1-nitroso-3-(α-D-ribofuranosyl) urea and 1-(2-chloroethyl)-1-nitroso-3-(β-D-ribofuranosyl) urea, possibly because of the reaction system being acidic, under which condition anomer-formation occurs.

After completion of the nitrosation reaction, the reaction mixture may, if necessary, be purified by treating with an ion exchange resin and the like to remove inorganic salts therefrom. The isolation of the two anomers may be made by any known or conventional method, for example, by a column chromatography. The filler for column chromatography may preferably be one with a low activity such as Frorigil (activated magnesium silicate) and silica gel. The nature of solvent used for the development in the column chromatography is not particularly limited so far as it makes the isolation of the desired product possible, but it is particularly preferred to use a solvent system comprising a first solvent selected from chloroform, methylene chloride, ethyl acetate, etc. and a second solvent selected from methanol, ethanol, acetone, etc. in appropriate proportions. Each fraction developed by the solvent is checked by thin layer chromatography to detect the desired fractions. All the fractions containing the desired compound thus detected are collected together and then distilled to remove the solvents and to leave the compound thus isolated.

The following Example illustrates the preparation and isolation of the novel nitrosourea compounds of this invention together with the preparation of the starting urea compounds.

By way of easier understanding, the route of reactions involved is schematically shown below:

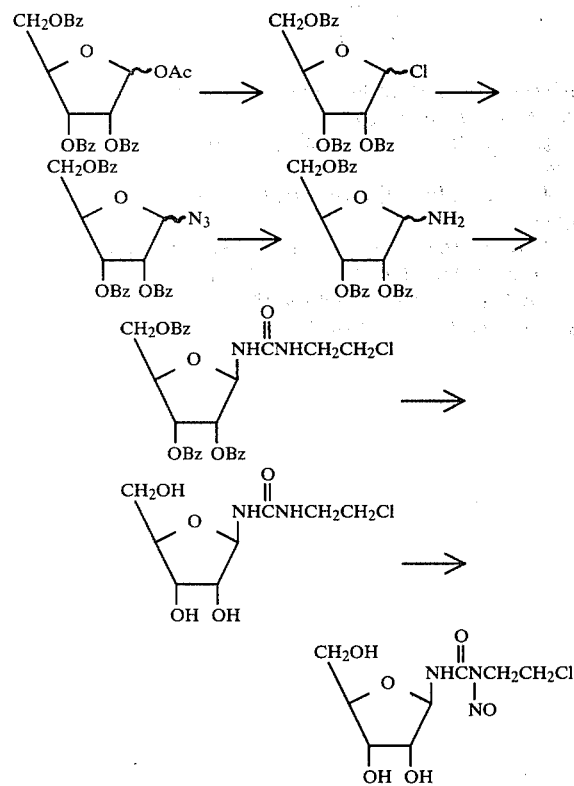

where Ac represents an acetyl group and Bz represents a benzoyl group.

EXAMPLE (1)
1-(2-chloroethyl)-3-(2,3,5-tri-O-benzoyl-β-D-ribofuranosyl) urea

1-O-Acetyl-2,3,5-tri-O-benzoyl-D-ribofuranosyl (30 g) was suspended in anhydrous ether (800 ml) and acetyl chloride (14 ml) was then added to the suspension. The chlorination was effected by blowing hydrogen chloride into the suspension at 0° C. followed by maintaining the suspension at −5° C. for 7 days. The reaction mixture was poured into a cooled sodium hydrogen carbonate solution and the resulting mixture was stirred and allowed to stand to separate it into layers. The ether layer was washed with a further amount of sodium hydrogen carbonate until the pH of the washings reached a value of 10 and then washed with cold water until the pH of the washings showed a neutral value. The ether solution was then dehydrated over calcium chloride and concentrated to yield 2,3,5-tri-O-benzyl-D-ribofuranosyl chloride (26 g) as a colourless syrup.

The chloride thus obtained was dissolved in anhydrous acetonitrile (300 ml), and sodium azide (28 g) was then added to the solution. The mixture was heated under reflux for 1.5 hours, filtered to remove insoluble matter and the resulting filtrate concentrated in vacuo to yield 2,3,5-tri-O-benzoyl-D-ribofuranosyl azide (25.5 g) as a pale yellow syrup.

The syrup was dissolved in ethyl acetate (200 ml) and Raney nickel T-4 (10 ml) was added thereto. The mixture was subjected to reduction in a stream of 3.4 kg/cm² of hydrogen for 1 hour, after which the catalyst was filtered off and the filtrate, after adding 2-chloroethyl isocyanate (3.6 ml) thereto, was kept at room temperature overnight. The reaction mixture was concentrated to a colorless syrup which was then crystallized from isopropylether to yield 1-(2-chloroethyl)-3-(2,3,5-tri-O-benzoyl-β-D-ribofuranosyl) urea (12.6 g) as crystals. Yield 37%.

Melting point: 167°–168° C.

$[\alpha]_D^{30}$: −36°(c=1.0, chloroform).

IR spectrum: 1730 (OCOPh), 1640 (CO), 1590 cm$^{-1}$ (NH).

Elemental analysis: Found: C 61.61, H 4.82, N 4.76, Cl 6.43%. Calculated for $C_{29}H_{27}N_2O_8Cl$. C 61.43, H 4.80, N 4.94, Cl 6.25%.

(2) 1-(2-chloroethyl)-3-(β-D-ribofuranosyl) urea

The crystals of 1-(2-chloroethyl)-3-(2,3,5-tri-O-benzoyl-β-D-ribofuranosyl) urea (3.0 g) obtained in step (1) above were partially dissolved in methanol (100 ml) and to the resulting suspension was added an 0.2 N methanolic solution of sodium methoxide (8 ml). Dissolution of the crystals in the methanol was completed by stirring the mixture at room temperature for 10 minutes. The resulting solution was stored in the cold for 7 days and then treated with 2 ml of a cation exchange resin "Amberlite" IR-120 (H+ form) (Amberlite is a trademark of Rohm and Haas Co.) to remove the sodium cation. The cation exchange resin was filtered off and the filtrate was concentrated in vacuo. The resulting residue was dissolved in water (100 ml) and washed three times with ethyl ether (50 ml each). The aqueous layer was concentrated in vacuo and the residue was crystallized from methanol to give 1-(2-chloroethyl)-3-(β-D-ribofuranosyl) urea (1.06 g) as crystals. Yield 81%.

Melting point: 166.5°–167.5° C.

$[\alpha]_D^{32}$: −26° (c=0.5, water).

IR spectrum: 1640 (CO), 1590 cm$^{-1}$ (NH).

Elemental analysis: Found: C 37.77, H 5.82, N 10.92, Cl 14.01%. Calculated for $C_8H_{15}N_2O_5Cl$. C 37.73, H 5.94, N 11.00, Cl 13.92%.

(3) 1-(2-chloroethyl)-1-nitroso-3-(α-D-ribofuranosyl) urea and
1-(2-chloroethyl)-1-nitroso-3-(β-D-ribofuranosyl) urea 1-(2-Chloroethyl)-3-(β-D-ribofuranosyl) urea (500 mg) which was obtained in step (2) above was dissolved in formic acid (4 ml) and to the resulting solution was added sodium nitrite (250 mg, 1.7 mol. equivalents) at 0° C. with subsequent stirring for 2 hours.

Thin layer chromatography of the reaction product on silica gel using chloroform-methanol (7:3 by volume) as the eluent gave spots at $R_f$ 0.44 and 0.51.

The reaction product was treated with 4 ml of a cation exchange resin "Amberlite" IR-120 (H+ form) and then concentrated in vacuo to give a yellow syrup. The syrup was subjected to column chromatography on a silica gel column packed with 50 g Wako gel C-300 (Wako gel is a trade name) using chloroform-methanol (20:1 by volume) as the eluent. The eluted fractions were analyzed by thin layer chromatography and fractions showing a spot at $R_f$ 0.44 thus detected were collected together and concentrated in vacuo. The resulting residue was crystallized from methanol-ethyl ether to yield 1-(2-chloroethyl)-1-nitroso-3-($\beta$-D-ribofuranosyl) urea (130 mg) as crystals. Yield 24%.

Melting point: 99° C.

$[\alpha]_D^{21}$: $-27.2°$ (c=0.5, pyridine).

Elemental analysis: Found: C 33.97, H 5.05, N 14.44, Cl 12.72%. Calculated for $C_8H_{14}N_3O_6Cl$. C 33.87, H 4.97, N 14.81, Cl 12.50%.

IR spectrum: 1720 (CO), 1540 (NH), 1505 cm$^{-1}$ (N-NO).

NMR spectrum (60 MHz, pyridine-d$_5$): $\delta$9.81 (d, 1H; J=9 Hz, NH), 3.56 (t, 2H; J=6.5 Hz, N-C$\underline{H}_2$CH$_2$Cl)

NMR spectrum (pyridine-d$_5$-D$_2$O): $\delta$6.33 (d, 1H; J=9.5 Hz, H-1).

Similarly, fractions eluted in the above column chromatography which showed a spot at $R_f$ 0.51 in the thin layer chromatographic analysis were collected together and concentrated in vacuo and the resulting residue was crystallized from methanol-ether to yield 1-(2-chloroethyl)-1-nitroso-3-($\alpha$-D-ribofuranosyl) urea (290 mg) as crystals. Yield 54%.

Melting point: 69°–71° C.

$[\alpha]_D^{25}$: $+47.2°$ (c=0.62, methanol).

Elemental analysis: Found: C 33.60, H 4.89, N 14.88, Cl 12.76%. Calculated for $C_8H_{14}N_3O_6Cl$. C 33.87, H 4.97, N 14.81, Cl 12.50%.

NMR spectrum (60 MHz, pyridine-d$_6$): $\delta$9.87 (d, 1H; J=8.5 Hz, NH)

6.25 (dd, 1H; J$_{NH}$=8.5 Hz, J$_{1,2}$=4 Hz, H, -1); 3.60 (t, 2H; J=6.5 Hz, N-C$\underline{H}_2$CH$_2$Cl.

NMR spectrum (pyridine-d$_5$-D$_2$O): $\delta$6.23 (d, 1H; J$_{1,2}$=4 Hz, H-1).

What I claim is:

1. A nitrosourea compound of the formula:

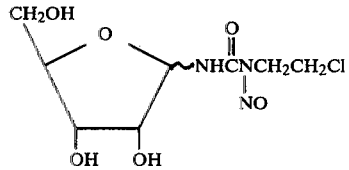

wherein $\sim$ represents a single bond which may be in either the $\alpha$- or $\beta$-position.

2. 1-(2-Chloroethyl)-1-nitroso-3-($\alpha$-D-ribofuranosyl) urea.

3. 1-(2-Chloroethyl)-1-nitroso-3-($\beta$-D-ribofuranosyl) urea.

4. A pharmaceutical composition comprising an effective amount of a nitrosourea compound as defined in claim 1 in association with a pharmaceutically acceptable excipient, carrier or diluent.

* * * * *